US008167823B2

United States Patent
Nycz et al.

(10) Patent No.: US 8,167,823 B2
(45) Date of Patent: May 1, 2012

(54) METHOD AND APPARATUS FOR ALIGNING AND SECURING AN IMPLANT RELATIVE TO A PATIENT

(75) Inventors: Jeffrey H. Nycz, Warsaw, IN (US); Christopher J. Nycz, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 377 days.

(21) Appl. No.: 12/358,664

(22) Filed: Mar. 24, 2009

(65) Prior Publication Data

US 2010/0249657 A1    Sep. 30, 2010

(51) Int. Cl.
 A61B 5/103 (2006.01)
 A61B 5/117 (2006.01)
 A61B 17/58 (2006.01)
 A61B 17/60 (2006.01)
 A61F 5/00 (2006.01)
 A61F 2/00 (2006.01)
 A61F 2/32 (2006.01)

(52) U.S. Cl. ............ 600/587; 600/595; 606/87; 606/91; 606/93; 606/99; 606/102; 623/22.11; 623/22.12

(58) Field of Classification Search .................. 600/587, 600/595; 606/87, 91, 93, 99, 102; 623/22.11, 623/22.12
See application file for complete search history.

(56) References Cited

U.S. PATENT DOCUMENTS

| | | | |
|---|---|---|---|
| 5,725,592 A * | 3/1998 | White et al. ............... 623/23.35 |
| 5,769,092 A * | 6/1998 | Williamson, Jr. ............. 128/898 |
| 5,880,976 A * | 3/1999 | DiGioia III et al. ............... 703/7 |
| 5,902,340 A * | 5/1999 | White et al. ................... 128/898 |
| 5,995,738 A * | 11/1999 | DiGioia et al. .................. 703/11 |
| 6,002,859 A * | 12/1999 | DiGioia et al. .................. 703/11 |
| 6,447,448 B1 * | 9/2002 | Ishikawa et al. .............. 600/300 |
| 6,583,630 B2 * | 6/2003 | Mendes et al. ................ 324/652 |
| 6,610,096 B2 * | 8/2003 | MacDonald ............... 623/18.11 |
| 6,702,821 B2 * | 3/2004 | Bonutti ........................... 606/88 |
| 6,711,431 B2 * | 3/2004 | Sarin et al. .................... 600/426 |
| 6,746,487 B2 * | 6/2004 | Scifert et al. ................ 623/22.12 |
| 6,810,753 B2 * | 11/2004 | Valdevit et al. .......... 73/862.045 |
| 6,821,299 B2 * | 11/2004 | Kirking et al. ............. 623/20.14 |
| 6,871,549 B2 | 3/2005 | Serra et al. |
| 7,001,393 B2 | 2/2006 | Schwenke et al. |
| 7,331,965 B2 | 2/2008 | Nielsen |

(Continued)

FOREIGN PATENT DOCUMENTS

EP    1563810 A1    8/2005

(Continued)

OTHER PUBLICATIONS

"c2a-Taper ceramic-on-ceramic articulation," Surgical Technique brochure. (2006, 2007) Biomet Orthopedics, Inc. (21 pages).

(Continued)

Primary Examiner — Sean Dougherty
(74) Attorney, Agent, or Firm — Harness Dickey

(57) ABSTRACT

A surgical apparatus includes an orientation sensor that detects an actual orientation of a surgical tool. The apparatus also includes an orientation feedback device that selectively provides an orientation feedback signal. Moreover, the apparatus includes a controller that causes the orientation feedback device to provide the orientation feedback signal when the actual orientation of the surgical tool detected by the orientation sensor is substantially equal to a predetermined target orientation of the surgical tool.

24 Claims, 3 Drawing Sheets

U.S. PATENT DOCUMENTS

| | | | | |
|---|---|---|---|---|
| 7,338,499 | B1* | 3/2008 | Kuczynski et al. | 606/102 |
| 7,377,182 | B2 | 5/2008 | Serra et al. | |
| 7,458,989 | B2* | 12/2008 | Banks et al. | 623/22.45 |
| 7,542,791 | B2* | 6/2009 | Mire et al. | 600/407 |
| 7,559,931 | B2* | 7/2009 | Stone | 606/91 |
| 7,636,595 | B2* | 12/2009 | Marquart et al. | 600/424 |
| 7,660,623 | B2* | 2/2010 | Hunter et al. | 600/424 |
| 7,780,681 | B2* | 8/2010 | Sarin et al. | 606/130 |
| 2002/0077540 | A1* | 6/2002 | Kienzle, III | 600/424 |
| 2002/0107523 | A1* | 8/2002 | Naughton et al. | 606/100 |
| 2003/0153829 | A1* | 8/2003 | Sarin et al. | 600/426 |
| 2003/0181987 | A1* | 9/2003 | Muirhead-Allwood | 623/22.15 |
| 2004/0034302 | A1* | 2/2004 | Abovitz et al. | 600/428 |
| 2004/0044295 | A1* | 3/2004 | Reinert et al. | 600/587 |
| 2004/0097952 | A1 | 5/2004 | Sarin et al. | |
| 2004/0102792 | A1* | 5/2004 | Sarin et al. | 606/151 |
| 2004/0117026 | A1* | 6/2004 | Tuma et al. | 623/18.11 |
| 2004/0171924 | A1* | 9/2004 | Mire et al. | 600/407 |
| 2004/0230199 | A1* | 11/2004 | Jansen et al. | 606/91 |
| 2004/0243148 | A1* | 12/2004 | Wasielewski | 606/130 |
| 2004/0254584 | A1* | 12/2004 | Sarin et al. | 606/102 |
| 2005/0021044 | A1* | 1/2005 | Stone et al. | 606/102 |
| 2005/0065617 | A1* | 3/2005 | Moctezuma de la Barrera et al. | 623/908 |
| 2005/0143828 | A1* | 6/2005 | Collins et al. | 623/18.11 |
| 2005/0203384 | A1* | 9/2005 | Sati et al. | 600/426 |
| 2005/0251026 | A1* | 11/2005 | Stone | 600/424 |
| 2006/0094958 | A1* | 5/2006 | Marquart et al. | 600/434 |
| 2006/0095047 | A1* | 5/2006 | de la Barrera | 606/102 |
| 2007/0149981 | A1 | 6/2007 | Bhattacharyya | |
| 2007/0179739 | A1 | 8/2007 | Donofrio et al. | |
| 2008/0133016 | A1 | 6/2008 | Heinz | |
| 2008/0249395 | A1* | 10/2008 | Shachar et al. | 600/409 |
| 2009/0099570 | A1* | 4/2009 | Paradis et al. | 606/91 |
| 2009/0138019 | A1* | 5/2009 | Wasielewski | 606/87 |
| 2009/0234217 | A1* | 9/2009 | Mire et al. | 600/407 |
| 2009/0318836 | A1* | 12/2009 | Stone et al. | 600/595 |
| 2009/0318930 | A1* | 12/2009 | Stone et al. | 606/102 |
| 2009/0318931 | A1* | 12/2009 | Stone et al. | 606/102 |
| 2010/0016705 | A1* | 1/2010 | Stone | 600/407 |
| 2010/0076505 | A1* | 3/2010 | Borja | 606/86 R |
| 2010/0100011 | A1* | 4/2010 | Roche | 600/587 |
| 2010/0137871 | A1* | 6/2010 | Borja | 606/91 |
| 2010/0249796 | A1 | 9/2010 | Nycz | |
| 2011/0060339 | A1 | 3/2011 | de Wekker | |

FOREIGN PATENT DOCUMENTS

| | | | |
|---|---|---|---|
| WO | WO 2004030556 A2 * | 4/2004 | |
| WO | WO-2004030556 A2 | 4/2004 | |
| WO | WO-2004112610 A2 | 12/2004 | |
| WO | WO 2004112610 A2 * | 12/2004 | |
| WO | WO-2007147235 A1 | 12/2007 | |
| WO | WO 2007147235 A1 * | 12/2007 | |

OTHER PUBLICATIONS

"Vision Acetabular Surgical Technique," brochure. 2001. Biomet Orthopedics, Inc. (16 pages).

International Search Report mailed Jun. 11, 2010 for PCT/US2010/028325 claiming benefit of U.S. Appl. No. 12/486,842, filed Jun. 18, 2009; which claims benefit of U.S. Appl. No. 12/358,664, filed Mar. 24, 2009.

International Preliminary Report mailed Oct. 6, 2011.

* cited by examiner

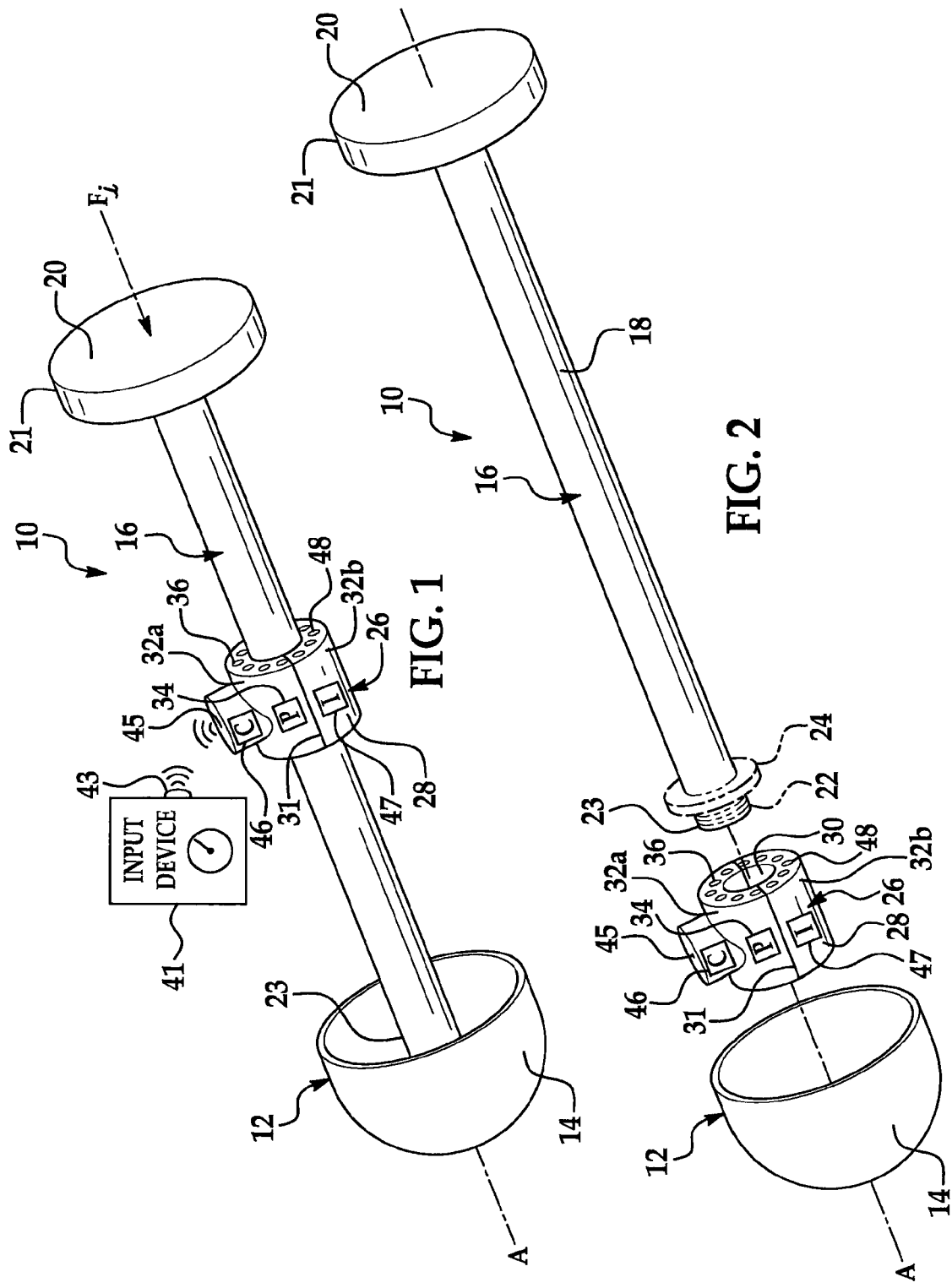

METHOD AND APPARATUS FOR ALIGNING AND SECURING AN IMPLANT RELATIVE TO A PATIENT

FIELD

The following relates to an implantable prosthesis and, more particularly, to a method and apparatus for aligning and securing an implant relative to a patient.

BACKGROUND

The statements in this section merely provide background information related to the present disclosure and may not constitute prior art.

Prosthetic joints can reduce pain due to arthritis, deterioration, deformation, and the like. Oftentimes, prosthetic joint assemblies include certain implantable prosthetic members that are fixed to the patient's anatomy. For instance, prosthetic hip joint assemblies often include an acetabular cup that is implanted and fixed to the patient's pelvis within the acetabulum. Once properly fixed to the pelvis, a liner may be received by the cup, and a femoral component may be moveably coupled within the liner.

Medical professionals often use impactor tools to implant and fix prosthetic members to the patient's anatomy. In the case of the acetabular cup, for instance, the surgeon may attach the cup to one end of the impactor tool and strike or otherwise apply a load to the impactor tool to drive the cup into the acetabulum. Then, the impactor tool is removed from the cup, leaving the cup in the desired location and orientation within the acetabulum. Fasteners can also be used to further secure the cup to the pelvis.

To ensure that the prosthetic member will be oriented in a desired position during the implantation procedure, the surgeon typically moves the impactor tool to a predetermined orientation relative to the patient's anatomy and applies the load while maintaining the impactor tool at this predetermined orientation. Certain measuring devices (e.g., goniometers, etc.) have been proposed for these purposes. Specifically, in the case of implanting an acetabular cup, the surgeon might orient the impactor tool such that the load axis is at a predetermined inclination angle relative to the median plane of the patient's body and/or such that the load axis is at a predetermined anteversion angle relative to the coronal plane of the patient's body. Thus, as the load is applied to the impactor tool, the cup is driven along and fixed at the predetermined inclination angle and/or the predetermined anteversion angle within the acetabulum.

However, measuring the orientation of the impactor tool in this manner can be tedious, time consuming, inconvenient and inaccurate. For instance, surgeons typically must repeatedly measure the orientation of the impactor tool because applying one or more loads to the impactor tool could move the impactor tool out of alignment with the predetermined orientation. Additionally, the impactor tool can be improperly aligned inadvertently due to human error. Furthermore, the goniometer or other measurement device is oftentimes separate from the impactor tool, and thus, the surgeon may need two hands to hold the impactor tool and measure its orientation. Also, blood, tissue or other matter can obscure the surgeon's ability to read the measurement device, which can lead to inaccuracies.

In addition, it can be difficult to know when the implantable prosthetic member has been driven far enough into bone or other tissue. For instance, a surgeon typically drives the acetabular cup far enough into the acetabulum to seat the cup against cancellous bone. However, it can be difficult to visually confirm that the cup is seated against the cancellous bone, and thus, surgeons typically rely on audible, tactile, or other non-visual cues to know the cup has been properly seated. For example, the surgeon repeatedly applies loads to the impactor tool to progressively drive the cup into the acetabulum until the surgeon hears a sound indicating that the cup is seated against cancellous bone. In other cases, loads are applied to the impactor tool until the surgeon feels a certain degree of bounce-back (i.e., displacement of the tool in a direction opposite to the vector of the impact force on the tool) indicating that the cup is seated against cancellous bone. However, the accuracy of these methods can be improved.

SUMMARY

A surgical apparatus is disclosed that includes an orientation sensor that detects an actual orientation of a surgical tool. The apparatus also includes an orientation feedback device that selectively provides an orientation feedback signal. Moreover, the apparatus includes a controller that causes the orientation feedback device to provide the orientation feedback signal when the actual orientation of the surgical tool detected by the orientation sensor is substantially equal to a predetermined target orientation of the surgical tool.

In another aspect, a method of implanting a prosthetic implant in a patient with an impactor tool is disclosed. The method includes determining a target orientation of the impactor tool necessary for moving the prosthetic implant to a target location. The method also includes automatically detecting an actual orientation of the impactor tool. Furthermore, the method includes automatically providing an orientation feedback signal when the actual orientation of the impactor tool is substantially equal to the target orientation of the impactor tool. Moreover, the method includes impacting the impactor tool while the actual orientation of the impactor tool is substantially equal to the target orientation of the impactor tool to move the prosthetic implant substantially toward the target location.

In still another aspect, an implanting assembly for implanting an acetabular cup of a prosthetic hip assembly in a patient is disclosed. The impactor assembly includes an impactor tool having an elongated shaft defining a load axis, a head at a first end, and a coupling mechanism at a second end for removably coupling to the acetabular cup. The impactor tool transfers a load due to impacting the impactor tool along the load axis to the acetabular cup. The implanting assembly additionally includes an implanting apparatus that is operatively coupled to the impactor tool. The implanting apparatus includes an orientation sensor that detects an actual inclination angle of the load axis relative to a median plane of the patient, and that detects an actual anteversion angle of the load axis relative to a coronal plane of the patient. The apparatus further includes an orientation feedback device that selectively provides an orientation feedback signal. Also, the apparatus device includes an impact sensor that detects an actual effect of impacting the impactor tool. The actual effect of impacting the impactor tool includes an actual impact force, an actual displacement of the impactor tool, and/or an actual acoustic effect of impacting the impactor tool. Additionally, the apparatus includes an impact feedback device that selectively provides an impact feedback signal. Moreover, the apparatus includes a controller that causes the orientation feedback device to provide the orientation feedback signal when the actual inclination angle is substantially equal to a predetermined target inclination angle and the actual anteversion angle is substantially equal to a predetermined target anteversion angle. The controller also causes the impact feedback device to provide the impact feedback signal when the actual effect of impacting the impactor tool detected by the impact sensor substantially matches or exceeds a predetermined target effect of impacting the impactor tool.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 1 is a perspective view of an implanting assembly according to the present disclosure;

FIG. 2 is an exploded view of the implanting assembly of FIG. 1;

DETAILED DESCRIPTION

Figures 3, 4:
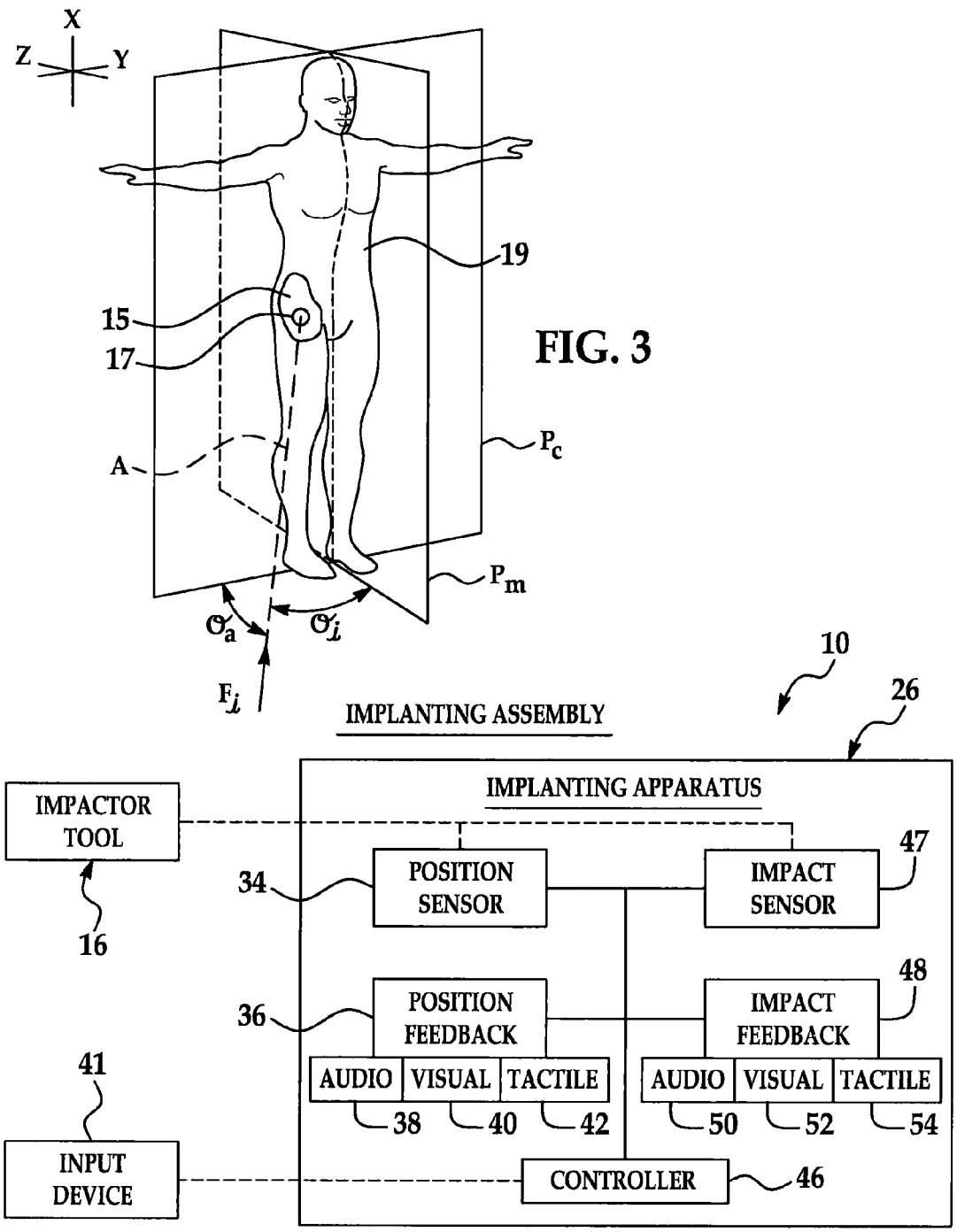
FIG. 3 is a perspective view of a patient, various reference planes, and a load axis of the implanting assembly of FIG. 1 relative to the various reference planes of the patient.
FIG. 4 is a schematic view of the implanting assembly of FIG. 1.

The following description is merely exemplary in nature and is not intended to limit the present disclosure, application, or uses. It should be understood that throughout the drawings, corresponding reference numerals indicate like or corresponding parts and features.

Referring initially to FIGS. 1, 2 and 4, an exemplary embodiment of an implanting assembly 10 is illustrated. As will be discussed, the implanting assembly 10 can be used for implanting any suitable prosthetic member 12. In the embodiments illustrated, the implanting assembly 10 is used to implant an acetabular cup 14. The acetabular cup 14 can be of any suitable type. Specifically, the implanting assembly 10 can be used to implant the acetabular cup 14 in a pelvis 15, within the acetabulum 17, of a patient 19 (FIG. 3). Thus, the implanting assembly 10 can be used in a process for replacing a hip joint with a prosthetic hip joint assembly.

The implanting assembly 10 can include an impactor tool 16, as shown in FIGS. 1 and 2. Generally, the impactor tool 16 can include an elongated shaft 18 having an enlarged striking plate or head 20 at a proximal or first end 21. The shaft 18 can be longitudinally straight so as to define an axis A. Alternately, the shaft 18 can be angled or curved to account for various anatomical shapes, surgical procedures, etc. Also, the enlarged head 20 can be substantially disk shaped and centered on the axis A. The distal or second end 23 of the shaft 18 can include a coupling mechanism 25 as shown in phantom in FIG. 2. In some embodiments, the coupling mechanism 25 can include a thread (shown in phantom at 22) and a projection (shown in phantom at 24). The thread 22 can enable the shaft 18 to be removably coupled to the acetabular cup 14 in a corresponding threaded hole (not shown) in the acetabular cup 14. Also, the projection 24 can abut the acetabular cup 14 for transferring loads from the shaft 18 to the acetabular cup 14, as will be described in greater detail below. It will be appreciated, however, that the impactor tool 16 can be removably coupled to the acetabular cup 14 in any suitable fashion.

Furthermore, the impactor tool 16 can be coupled to the acetabular cup 14 such that the shaft 18 and the acetabular cup 14 both extend along the axis A.

As will be described, in order to implant the acetabular cup 14 in the patient 19, a load $F_i$ (FIG. 1) is applied to the head 20 of the impactor tool 16. The surgeon can apply the load $F_i$ with a mallet or other manual tool or with an automated tool. The shaft 18, in turn, transfers the load $F_i$ along the axis A to the acetabular cup 14. Thus, the acetabular cup 14 is driven progressively into the acetabulum 17 of the pelvis 15 of the patient 19 (FIG. 3) with each application of the load $F_i$.

It will be appreciated that the load $F_i$ transfers along the axis A to the acetabular cup 14. Thus, the axis A corresponds to the load axis A of the implanting assembly 10. It will also be appreciated that the impactor tool 16 could include a curved or offset axis A and that the load $F_i$ could be a rotational (i.e., angular) load without departing from the scope of the present disclosure.

The implanting assembly 10 can also include an implanting apparatus 26 (FIGS. 1, 2 and 4). As shown in FIGS. 1 and 2, the implanting apparatus 26 can include a housing 28. The housing 28 can be operatively coupled to the impactor tool 16. In some embodiments, the housing 28 can be removably coupled to the shaft 18 of the impactor tool 16 such that the implanting apparatus 26 extends substantially parallel to the axis A of the shaft 18. Specifically, the housing 28 can be substantially cylindrical in shape with a passage 30 extending parallel and concentric to the axis A. The passage 30 receives the shaft 18 to fixedly couple the housing 28 to the tool 16 in a fixed position relative to the axis A.

Furthermore, the housing 28 can include a seam 31 extending substantially parallel to the axis A. The seam 31 separates a first portion 32a from a second portion 32b of the housing 28. Thus, the first and second portions 32a, 32b can separate along the seam 31 to remove the housing 28 from the shaft 18. In some embodiments, the housing 28 can have a clam shell design with a hinge (not shown) for hingeably attaching the first and second portions 32a, 32b of the housing 28.

It will be appreciated that the housing 28 can fix to the shaft 18 in any suitable fashion, such as an interference fit, a taper lock between the shaft 18 and the inner surface of the passage 30, and the like. Also, the shaft 18 can include a recess (not shown) that receives the housing 28 such that the housing 28 is in a fixed position relative to the axis A. Accordingly, the implanting apparatus 26 can removably couple to preexisting, commercially available impactor tools 16, such as a Ring-Loc® Inserter (Part No. S313141) or a Magnum Inserter (Part No. 313131), commercially available from Biomet, Inc. of Warsaw, Ind.

Furthermore, it will be appreciated that the implanting apparatus 26 can be operatively coupled to the impactor tool 16 at any suitable location, including the head 20. It will also be appreciated that the seam 31 is optional, and the implanting apparatus 26 can be configured to slide on to the shaft 18 in a direction substantially parallel to the axis A (see FIG. 2). In addition, it will be appreciated that the implanting apparatus 26 can be integrally coupled to the impactor tool 16 such that the implanting apparatus 26 and the impactor tool 16 are monolithic. For instance, the implanting apparatus 26 can be incorporated directly in the shaft 18 and/or the head 20 or any other suitable portion of the tool 16. Also, in some embodiments, the implanting apparatus 26 may be configured so that the apparatus 26 can be operably coupled to surgical tools other than an implanting apparatus 26 for use in any other suitable surgical procedure.

As shown in FIGS. 1, 2 and 4, the implanting apparatus 26 can include an orientation sensor 34. The orientation sensor 34 can be encapsulated within the housing 28. In other embodiments, the orientation sensor 34 is remote from the impactor tool 16. As will be discussed, the orientation sensor 34 can detect an actual orientation of the impactor tool 16. More specifically, the orientation sensor 34 can be an accelerometer that is able to detect the orientation of the impactor tool 16 relative to a reference vector. In some embodiments, for instance, the orientation sensor 34 detects the vector of the force of gravity as a reference vector to detect the orientation of the impactor tool 16 in space and relative to the patient. More specifically, the orientation sensor 34 detects the orientation of the axis A relative to the vector of the force of gravity to detect the orientation of the tool 16. In some embodiments, the orientation sensor 34 detects acceleration about three separate orthogonal axes X, Y, Z (FIG. 3) in order to detect the orientation of the impactor tool 16. Specifically, the orientation sensor 34 detects the orientation of the axis A relative to the coordinate system X, Y, Z, as will be discussed in greater detail below. It will be appreciated that the orientation sensor 34 could be of any suitable type other than an accelerometer. Also, it will be appreciated that the orientation sensor 34 can be an accelerometer that detects accelerations about any number (e.g., two) of axes.

Furthermore, the implanting apparatus 26 can include an orientation feedback device 36. The feedback device 36 can be encapsulated within the housing 28, or in other embodiments, the feedback device 36 is remote from the housing 28. As will be described, the orientation feedback device 36 can selectively provide an orientation feedback signal when the actual orientation of the impactor tool 16 is substantially equal to a predetermined target orientation. Accordingly, as will be described in greater detail below, the feedback signal provided by the orientation feedback device 36 automatically indicates to the surgeon that the impactor tool 16 is in the target orientation such that the cup 14 can be properly positioned and implanted for added convenience and accuracy.

As represented in FIG. 4, the orientation feedback device 36 can include an audible feedback device 38 that emits an audible feedback signal. For instance, the audible feedback device 38 can include a speaker that emits a preprogrammed sound when the impactor tool 16 is in the target orientation. Furthermore, the orientation feedback device 36 can include a visual feedback device 40 that emits a visual feedback signal. For instance, the visual feedback device 40 can include one or more lights, such as LED lights, for emitting a preprogrammed light pattern when the impactor tool 16 is in the target orientation. Additionally, the orientation feedback device 36 can include a tactile feedback device that selectively emits a tactile feedback signal when the impactor tool 16 is in the target orientation. For instance, the tactile feedback device 42 can include a vibration motor that selectively vibrates the housing 28 and the impactor tool 16 when the impactor tool 16 is in the target orientation.

It will be appreciated that the orientation feedback device 36 can provide any suitable feedback signal. Also, it will be appreciated that the feedback signal can be seen, heard, and felt simultaneously, and this redundancy can increase accuracy and convenience. Thus, for instance, if the visual feedback device 40 becomes covered in blood or tissue during use, the audible and/or tactile feedback device 38, 42 can adequately provide the feedback signal. However, it will be appreciated that the orientation feedback device 36 can include any number of feedback devices 38, 40, 42 or any other suitable feedback device without departing from the scope of the present disclosure.

Moreover, as illustrated in FIG. 4, the implanting apparatus 26 can include a controller 46. The controller 46 can include various components, such as a microprocessor, memory, and the like. The controller 46 can be encapsulated within the housing 28 of the implanting apparatus 26, or the controller 46 can be at least partially provided in a remote device, such as a separate computerized system. The controller 46 can be in communication with the orientation sensor 34 and the orientation feedback device 36. Accordingly, as will be discussed, the controller 46 causes the orientation feedback device 36 to selectively provide the respective orientation feedback signal(s) when the actual orientation of the impactor tool 16 detected by the orientation sensor 34 is substantially equal to a predetermined target orientation of the impactor tool 16.

More specifically, with reference to FIG. 3, the medical professional can analyze the pelvis 15 and other anatomical features of the patient 19 to determine a desired final, target location (i.e., target position, target orientation) for the acetabular cup 14 within the acetabulum 17, which will provide the patient 19 with sufficient stability, support, etc. The implanting assembly 10 can be used to properly orient the impactor tool 16 such that the impactor tool 16 accurately drives the acetabular cup 14 toward this desired target location. For instance, the surgeon can predetermine how the load axis A of the impactor tool 16 should be oriented relative to a reference coordinate system such that the impactor tool 16 drives the acetabular cup 14 into the predetermined target location. For purposes of discussion, this will be referred to as the predetermined target orientation of the impactor tool 16. It will be appreciated that the target orientation of the impactor tool 16 substantially corresponds to the trajectory or path of the acetabular cup 14 as it is driven into the acetabulum 17 by the impactor tool 16.

As shown in FIG. 3, the predetermined target orientation of the impactor tool 16 can be the orientation of the load axis A relative to a median plane $P_m$ (i.e., sagittal plane) and a coronal plane $P_c$ (i.e., frontal plane) of the patient 19. Specifically, the surgeon can determine a particular target inclination angle $\theta_i$ of the load axis A relative to the median plane $P_m$ and/or a particular anteversion angle $\theta_a$ of the load axis A relative to the coronal plane $P_c$ necessary for the impactor tool 16 to drive the acetabular cup 14 into the final location within the pelvis 19.

It will be appreciated that the predetermined target orientation can be expressed as a range of values. In some embodiments, for instance, the target inclination angle $\theta_i$ is at least approximately 35° and at most approximately 55°. Also, in some embodiments, the target anteversion angle $\theta_a$ is at least 10° and at most 20°. Furthermore, in some embodiments, the target inclination angle $\theta_i$ is approximately 45°. Additionally, in some embodiments, the target anteversion angle $\theta_a$ is approximately 15°. As will be discussed, the implanting apparatus 26 can include one or more selectable preprogrammed target orientations, which is/are stored in memory, and/or the predetermined target orientation can manually set by the user.

It will be appreciated that the target inclination and anteversion angles $\theta_i$, $\theta_a$ can be determined for each individual patient 19 according to the anatomical structure of the patient 19 and/or other factors. It will also be appreciated that the target inclination and anteversion angles $\theta_i$, $\theta_a$ can be of any suitable values. Furthermore, it will be appreciated that the implantation assembly 10 can be used to detect and confirm any suitable orientation of the impactor tool 16 relative to any suitable reference plane, axis, etc. It will be appreciated that the reference plane, axis, etc. can be separate from the patient 19, or in other embodiments, the reference plane, axis, etc. can be associated directly with the anatomy of the patient 19.

For instance, the surgeon can input the location, orientation, etc. of certain anatomical features into a computerized system, and this data can be used as reference data or as a coordinate system to detect the actual orientation of the impactor tool 16 as will be discussed.

Thus, to implant the acetabular cup 14, the surgeon dislocates the hip joint of the patient 19, performs any necessary reaming of the acetabulum 17 of the patient 19, and mounts the acetabular cup 14 to the impactor tool 16 as discussed above. The surgeon also determines the target inclination angle $\theta_i$, and the anteversion angle $\theta_a$ of the impactor tool 16. Then, as the surgeon moves the impactor tool 16 generally into position to implant the cup 14, the orientation sensor 34 detects the actual orientation of the load axis A of the impactor tool 16. The orientation feedback device 36 provides one or more feedback signals when the load axis A is substantially aligned with the predetermined target inclination angle $\theta_i$ and the predetermined target anteversion angle $\theta_a$. Once the feedback signals are provided, the surgeon knows that the impactor tool 16 is properly oriented, and the surgeon can begin applying the load $F_i$ to the head 20 of the impactor tool 16, thereby driving the cup 14 into the acetabulum 17 of the patient 19.

It will be appreciated that the implanting apparatus 26 can be configured to detect any suitable orientation other than the inclination angle $\theta_i$ and the anteversion angle $\theta_a$. Also, it will be appreciated that the orientation feedback device 36 can provide separate feedback signals for the inclination angle $\theta_i$ and the anteversion angle $\theta_a$. Furthermore, the implanting apparatus 26 can store in memory one or more default target inclination angles $\theta_i$ and/or target anteversion angles $\theta_a$.

Additionally, in some embodiments, the implanting apparatus 26 can include various controls for manually setting the target inclination angle $\theta_i$ and/or target anteversion angle $\theta_a$. For instance, the implanting assembly 10 can include an input device 41 (FIGS. 1 and 4) for manually setting the target orientation of the impactor tool 16. More specifically, the input device 41 can include buttons, dials, a display, and other features for setting the target inclination angle $\theta_i$, the target anteversion angle $\theta_a$, or any other setting for the implanting assembly 10. The input device 41 can be integrally coupled to the housing 28, and/or the input device 41 can be separate and remote from the housing 28 of the apparatus 26. For instance, the input device 41 can be in wireless communication with the implanting apparatus 26. For instance, as shown in FIG. 1, the input device 41 can include a wireless transmitter 43, and the implanting apparatus 26 can include a wireless receiver 45. The receiver 45 receives wireless signals from the transmitter 43 to thereby set the target orientation of the load axis A. For instance, the input device 41 can include a switch for choosing between multiple (e.g., three) different preset target orientations (e.g., a first non-adjustable range, a second non-adjustable range, and a third non-adjustable range). Also, in some embodiments, the input device 41 can include an alphanumeric keypad for manually inputting and setting a particular target orientation.

Furthermore, in some embodiments, the input device 41 can include the orientation feedback device 36. For instance, the input device 41 can include a speaker of the audible feedback device 38 or any other suitable component of the orientation feedback device 36.

Thus, the implanting apparatus 26 can allow the surgeon to implant the acetabular cup 14 more conveniently and with greater accuracy. It will be appreciated that the implanting apparatus 26 can provide feedback to the surgeon before the input load $F_i$ is applied and while the acetabular cup 14 is being driven into the acetabulum 17. Accordingly, the acetabular cup 14 can be more easily and accurately placed into the target location within the pelvis 15.

However, it can be difficult for the surgeon to know when the acetabular cup 14 is fully seated in the pelvis 15. Thus, the implanting apparatus 26 can further include an impact sensor 47 (FIGS. 1, 2 and 4). As will be described, the impact sensor 47 can detect an actual effect of impacting the impactor tool 16. For instance, the impact sensor 47 can be configured to detect an actual impact force $F_i$ on the head 20 of the impactor tool 16. Furthermore, the impact sensor 47 can detect an actual displacement of the impactor tool 16 when the load $F_i$ is applied to the head 20. In addition, the impact sensor 47 can detect an actual acoustic effect occurring when the load $F_i$ is applied. It will be appreciated that the impact sensor 47 can be configured to detect any suitable effect of applying the load $F_i$. The impact sensor can include any suitable component, such as an accelerometer and/or a piezoelectric sensor, for detecting the actual impact effect. It will be appreciated that the orientation sensor 34 and the impact sensor 47 can rely on the same components, such as a common accelerometer, for the respective functions.

In addition, the implanting apparatus 10 can include an impact feedback device 48 (FIG. 4). Generally, the impact feedback device 48 provides a feedback signal when the actual effect of applying the load $F_i$ detected by the impact sensor 47 substantially matches a predetermined target impact effect. More specifically, as will be discussed, the surgeon can predetermine a target impact effect (e.g., a predetermined impact force $F_i$, an amount of displacement, an acoustic effect, etc.) that correlates to a condition in which the acetabular cup 14 is fully seated in the acetabulum 17. Then, the controller 46 can cause the impact feedback device 48 to provide the respective feedback signal when the actual impact effect substantially matches the predetermined target impact effect. Thus, the impact feedback device 48 can inform the surgeon that the acetabular cup 14 has been driven sufficiently deep enough into the acetabulum 17 of the patient 19.

More specifically, when the acetabular cup 14 is driven into the acetabulum 17 and hits cortical bone, the amount of bounce back (i.e., displacement) of the impactor tool 16 in a direction opposite to the vector of the load $F_i$ may change significantly. This predetermined amount of displacement can be stored in memory as the target impact effect of applying the load $F_i$, and the impact feedback device 48 can provide the feedback signal when the actual displacement of the impactor tool 16 is substantially equal to or exceeds the target displacement, thereby indicating that the acetabular cup 14 has reached the cortical bone of the pelvis 15. Likewise, the target impact effect can be a predetermined threshold amount of force, acoustic effect, or any other suitable target effect indicative of the acetabular cup 14 impacting the cortical bone. Moreover, in some embodiments, the input device 41 can be used to manually select a preset target impact effect or to manually set an individual target impact effect as discussed above.

It will be appreciated if the impact feedback device 48 can include any suitable device, such as an audible feedback device 50, a visual feedback device 52, and/or a tactile feedback device 54. The audible feedback device 50 provides an audible feedback signal, and can include a speaker or any other suitable device for providing an audible feedback signal. The visual feedback device 52 provides a visual feedback signal, and can include one or more lights, such as LED lights, for providing a visual feedback signal. Also, the tactile feedback device 54 provides a tactile feedback signal and can include a vibration motor that selectively provides a tactile feedback signal.

Figure 5:
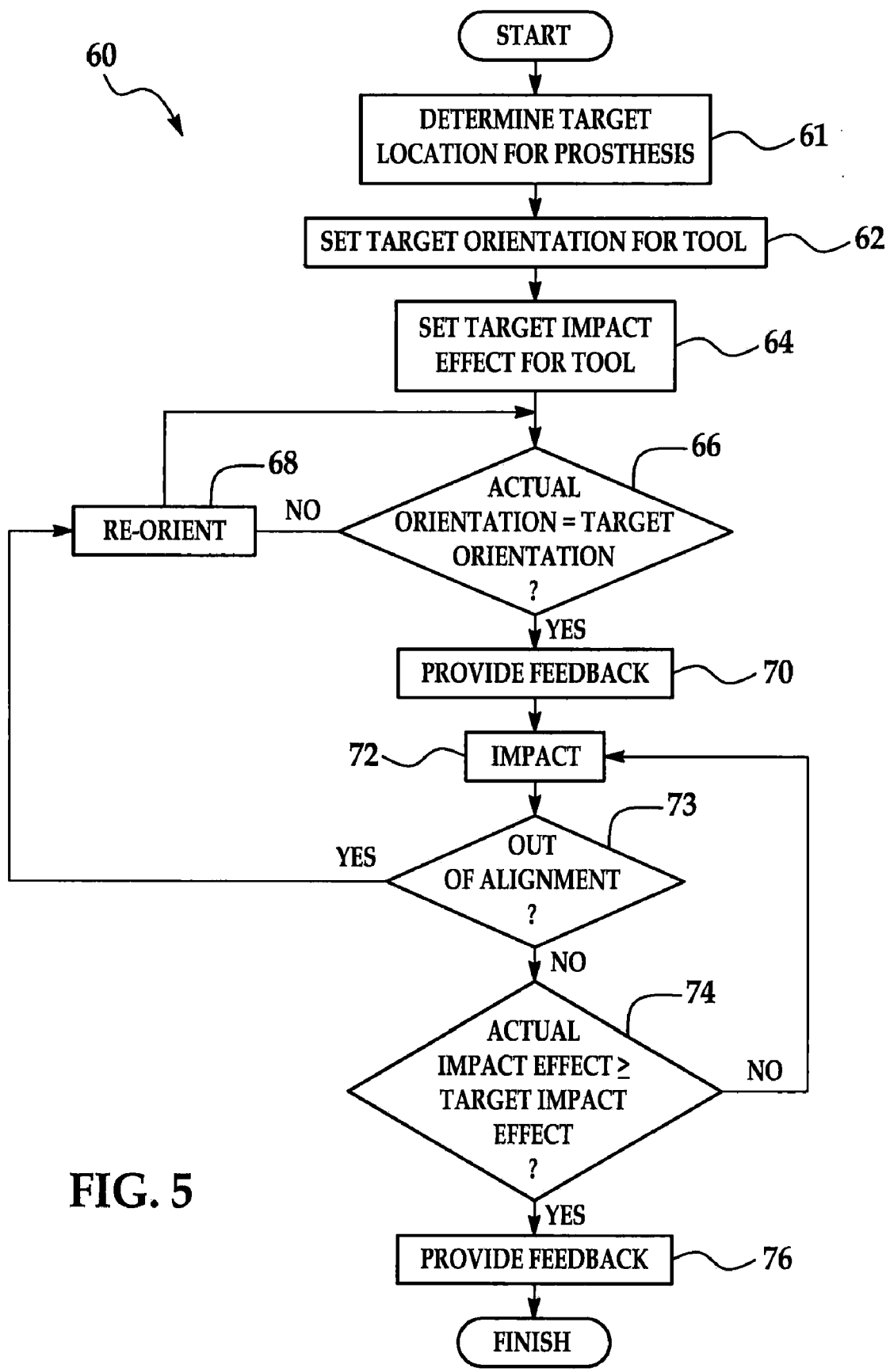
FIG. 5 is a flowchart illustrating a method of implanting a prosthetic implant using the implanting assembly of FIG. 1.

Thus, referring to FIG. 5, an exemplary embodiment of a method of implanting the acetabular cup 14 will be discussed in greater detail. The method 60 begins in block 61, in which the target location of the acetabular cup 14 is determined. More specifically, the surgeon analyzes the pelvis 15 and other anatomical features of the patient 19 and determines where the acetabular cup 14 should be implanted (i.e., the target location of the acetabular cup 14) within the acetabulum 17. Block 61 can include selecting a particular inclination angle $\theta_i$ and/or a particular anteversion angle $\theta_a$ of the axis A of the acetabular cup 14.

Then, in block 62, the surgeon determines a target orientation for the impactor tool 16 necessary to drive the acetabular cup 14 into the target location determined in block 61. As discussed above, the surgeon can use the input device 41 to manually input a target orientation for the impactor tool 16, or the surgeon can use the input device 41 to select one of the various default target orientations for the impactor tool 16. Also, the input device 41 can automatically calculate and set the target orientation of the impactor tool 16 based on various parameters input by the surgeon. In some embodiments, the target orientation can be set to any suitable value(s) for high precision.

Furthermore, in block 64, the surgeon determines a target impact effect for the impactor tool 16. As discussed above, the input device 41 can be used to set the target impact effect necessary for achieving the target location selected in block 61. Also, the surgeon can use the input device 41 to select one of the various default target impact effects, or the input device 41 can automatically calculate and set the target impact effect based on various parameters input by the surgeon. Moreover, the target impact effect can be set to any suitable value(s) for high precision.

Then, as the surgeon moves the impactor tool 16, it is determined in decision block 66 whether the actual orientation of the load axis A is substantially equal to or within the predetermined range of the target orientation set in block 62. If the actual orientation is substantially equal to or within the range of the target orientation, then in block 70, the orientation feedback device 36 provides the respective feedback signal(s) described above. However, if the actual orientation does not substantially equal or is outside the range of the target orientation, then in block 68, the surgeon re-orients the impactor tool 16 until the actual orientation is substantially equal to or within the range of the target orientation (i.e., decision block 66 answered affirmatively) and the orientation feedback signal(s) is/are provided.

Then, in block 72, the surgeon begins applying the load $F_i$ to the head 20 of the impactor tool 16. The load $F_i$ can be applied with a manual tool, such as a mallet, or an automated tool can be used to apply the load $F_i$.

In some embodiments, the surgeon strikes the head 20 of the impactor tool 16 repeatedly to progressively drive the cup 14 deeper into the acetabulum 17. Because each impact may cause the impactor tool 16 to move out of alignment with the target orientation set in block 62, the method 60 includes decision block 73, wherein it is determined whether the load axis A of the impactor tool 16 has moved out of alignment from the target orientation. If decision block 73 is answered affirmatively, block 68 follows, and the surgeon reorients the impactor tool 16 until the load axis A is substantially aligned with the target orientation. Once the impactor tool 16 is properly reoriented, the feedback signal is again provided in block 70, and the surgeon can continue to impact the tool 16. However, assuming that the actual orientation of the load axis A remains in alignment with the target orientation set in block 62 (i.e., decision block 73 answered negatively), decision block 74 follows.

In decision block 74, it is determined whether the actual impact effect substantially matches or exceeds a threshold of the target impact effect set in block 64. If the actual impact effect is substantially different from the target impact effect, then block 72 occurs, and the surgeon further applies the load $F_i$ supplied to the head 20 of the impactor tool 16. However, once the impact sensor 47 detects that the actual impact effect substantially matches or exceeds the target impact effect, then the impact feedback device 48 provides the respective feedback signal in block 76, and the surgeon is aware that the cup 14 is in the target location predetermined in block 61. It will be appreciated that the impact feedback signal can be provided simultaneously with the orientation feedback signal so that the surgeon knows that the acetabular cup 14 is correctly located in the desired target location within the acetabulum 17.

In some embodiments, once the feedback signals have been provided, they can be manually turned off. For instance, if the feedback signal is a light, then the surgeon has the ability to turn off the light. Thus, the surgeon has greater control over the feedback signal. Also, if the surgeon wishes to re-confirm that the impactor tool 16 is properly oriented or that the acetabular cup 14 is properly seated, the surgeon can turn off the respective feedback signal and check whether the feedback signal is provided again.

Accordingly, the implanting assembly 10 provides a convenient and accurate means for orienting the impactor tool 16 and for implanting the acetabular cup 14. The implanting assembly 10 also ensures that the acetabular cup 14 will be seated in the desired location within the pelvis 15. As such, the prosthetic joint assembly is more likely to provide adequate support and stability to the patient 19.

Moreover, the foregoing discussion discloses and describes merely exemplary embodiments of the present disclosure. One skilled in the art will readily recognize from such discussion, and from the accompanying drawings and claims, that various changes, modifications and variations may be made therein without departing from the spirit and scope of the disclosure as defined in the following claims. For instance, the sequence of the blocks of the method described herein can be changed without departing from the scope of the present disclosure.

What is claimed is:

1. A surgical apparatus comprising:
an orientation sensor that detects an actual orientation of a surgical tool;
a plurality of orientation feedback devices, each of the plurality of orientation feedback devices providing an orientation feedback signal, the plurality of orientation feedback devices including at least two of a visual feedback device, an audible feedback device, and a tactile feedback device;
a controller that causes the plurality of orientation feedback devices to each provide the respective orientation feedback signal when the actual orientation of the surgical tool detected by the orientation sensor is substantially equal to a predetermined target orientation of the surgical tool; and
an impact sensor that detects an actual acoustic effect of impacting the surgical tool, an impact feedback device that selectively provides an impact feedback signal, and wherein the controller causes the impact feedback device to provide the impact feedback signal when the actual acoustic effect of impacting the surgical tool detected by the impact sensor substantially matches a predetermined target acoustic effect of impacting the surgical tool.

2. The surgical apparatus of claim 1, wherein the orientation sensor includes an accelerometer.

3. The surgical apparatus of claim 2, wherein the orientation sensor includes an accelerometer that detects accelerations about three axes that are orthogonal to each other.

4. The surgical apparatus of claim 1, further comprising a housing, which encapsulates the orientation sensor, wherein the housing is removably coupled to the surgical tool.

5. The surgical apparatus of claim 4, wherein the housing has a first portion and a second portion that are hingeably attached so as to have a clam shell construction, the housing being removeably coupled to the surgical tool, wherein the surgical tool includes a head operable to be impacted for driving the surgical tool in a direction, and wherein the orientation feedback device is oriented toward the head to be viewable by the user when impacting the head.

6. The surgical apparatus of claim 1, further comprising a housing, which encapsulates the orientation sensor, wherein the housing is integrally coupled to the surgical tool, such that the housing and the surgical tool are monolithic.

7. The surgical apparatus of claim 1, wherein the impact sensor includes a piezoelectric sensor.

8. The surgical apparatus of claim 1, further comprising an input device for changing the predetermined target orientation.

9. The surgical apparatus of claim 8, wherein the input device is in wireless communication with the controller for changing the predetermined target orientation.

10. The surgical apparatus of claim 1, wherein the orientation sensor detects the actual orientation of a load axis of the surgical tool to thereby detect an actual inclination angle of the load axis relative to a median plane of the patient, and wherein the controller causes the plurality of orientation feedback devices to each provide the respective orientation feedback signal when the actual inclination angle of the load axis relative to the median plane is substantially equal to a predetermined target inclination angle of the load axis relative to the median plane.

11. The surgical apparatus of claim 10, wherein the predetermined target inclination angle is between about 35 degrees to 55 degrees.

12. The surgical apparatus of claim 11, wherein the predetermined target inclination angle is approximately 45 degrees.

13. The surgical apparatus of claim 1, wherein the orientation sensor detects the actual orientation of a load axis of the surgical tool to thereby detect an actual anteversion angle of the load axis relative to a coronal plane of the patient, and wherein the controller causes the plurality of orientation feedback devices to each provide the respective orientation feedback signal when the actual anteversion angle of the load axis relative to the coronal plane is substantially equal to a predetermined target anteversion angle of the load axis relative to the coronal plane.

14. The surgical apparatus of claim 13, wherein the predetermined target anteversion angle is between about 10 degrees and 20 degrees.

15. The surgical apparatus of claim 14, wherein the predetermined target anteversion angle is approximately 15 degrees.

16. The surgical apparatus of claim 1, wherein the orientation sensor detects an actual orientation of an impactor tool that transfers a load to a prosthetic implant for implanting the prosthetic implant in a patient.

17. The surgical apparatus of claim 1, wherein the plurality of orientation feedback devices include each of the audible feedback device and the tactile feedback device.

18. The surgical apparatus of claim 1, wherein the impact feedback device provides at least two of a visual feedback signal, an audible feedback signal, and a tactile feedback signal.

19. The surgical apparatus of claim 1, wherein the surgical tool is operable to be impacted to drive the surgical tool along a first direction, and
wherein the impact sensor detects an actual displacement of the surgical tool along a second direction due to impacting the surgical tool, wherein the second direction is different from the first direction.

20. The surgical apparatus of claim 19, wherein the second direction is substantially opposite the first direction.

21. A method of implanting a prosthetic implant in a patient with an impactor tool comprising:
determining a target orientation of the impactor tool necessary for moving the prosthetic implant to a target location;
automatically detecting an actual orientation of the impactor tool;
automatically providing an orientation feedback signal when the actual orientation of the impactor tool is substantially equal to the target orientation of the impactor tool;
impacting the impactor tool while the actual orientation of the impactor tool is substantially equal to the target orientation of the impactor tool to move the prosthetic implant substantially toward the target location;
automatically detecting an actual acoustic impact effect of impacting the impactor tool; and
automatically providing an impact feedback signal when the actual acoustic impact effect substantially matches a predetermined target acoustic impact effect.

22. The method of claim 21, wherein automatically providing the impact feedback signal includes automatically providing at least two of a visual feedback signal, an audible feedback signal, and a tactile feedback signal.

23. An impactor assembly for implanting an acetabular cup of a prosthetic hip assembly in a patient, the impactor assembly comprising:
an impactor tool having an elongated shaft defining a load axis, a head at a first end, and a coupling mechanism at a second end for removably coupling to the acetabular cup, the impactor tool for transferring a load from impacting the impactor tool along the load axis to the acetabular cup; and
an implanting apparatus that is operatively coupled to the impactor tool, the implanting apparatus comprising:
an orientation sensor that detects an actual inclination angle of the load axis relative to a median plane of the patient and that detects an actual anteversion angle of the load axis relative to a coronal plane of the patient;
a plurality of orientation feedback devices, each of the plurality of orientation feedback devices providing an orientation feedback signal, the plurality of orientation feedback devices including a visual feedback device, an audible feedback device, and a tactile feedback device;
an impact sensor that detects an actual effect of impacting the impactor tool, the actual effect of impacting the impactor tool including an actual acoustic effect of impacting the impactor tool;
an impact feedback device that selectively provides an impact feedback signal; and a controller that causes the plurality of orientation feedback devices to each provide the respective orientation feedback signal when the actual inclination angle is substantially equal to a predetermined target inclination angle and the actual anteversion angle is substantially equal to a predetermined target anteversion angle, the controller also causing the impact feedback device to provide the impact feedback signal when the actual acoustic effect of impacting the impactor tool detected by the impact sensor substantially matches a predetermined target acoustic effect of impacting the impactor tool.

24. The implanting assembly of claim 23, wherein the controller simultaneously causes the plurality of orientation feedback devices to each provide the respective orientation feedback signal and the impact feedback device to provide the impact feedback signal.

* * * * *